United States Patent
Rosnov

(10) Patent No.: US 8,816,846 B2
(45) Date of Patent: Aug. 26, 2014

(54) INTERNET-PROTOCOL BASED TELEMETRY PATIENT MONITORING SYSTEM

(75) Inventor: Brian Scott Rosnov, Melrose, MA (US)

(73) Assignee: Koninklijke Philips N.V., Eindhoven (NL)

( * ) Notice: Subject to any disclaimer, the term of this patent is extended or adjusted under 35 U.S.C. 154(b) by 2035 days.

(21) Appl. No.: 11/720,109

(22) PCT Filed: Nov. 4, 2005

(86) PCT No.: PCT/IB2005/053632
§ 371 (c)(1),
(2), (4) Date: May 24, 2007

(87) PCT Pub. No.: WO2006/056896
PCT Pub. Date: Jun. 1, 2006

(65) Prior Publication Data
US 2007/0255120 A1    Nov. 1, 2007

Related U.S. Application Data

(60) Provisional application No. 60/630,997, filed on Nov. 24, 2004.

(51) Int. Cl.
*G08B 1/08*    (2006.01)
(52) U.S. Cl.
USPC ..................................... 340/539.12
(58) Field of Classification Search
USPC ................. 340/539.12, 539.11, 573.1, 13.24; 600/300
See application file for complete search history.

(56) References Cited

U.S. PATENT DOCUMENTS

| | | | |
|---|---|---|---|
| 5,944,659 A | 8/1999 | Flach et al. | |
| 6,416,471 B1 | 7/2002 | Kumar et al. | |
| 7,088,233 B2 * | 8/2006 | Menard | 340/539.1 |
| 7,590,589 B2 * | 9/2009 | Hoffberg | 705/37 |
| 2002/0158775 A1 | 10/2002 | Wallace | |
| 2003/0177437 A1 * | 9/2003 | Wu | 714/776 |
| 2004/0109429 A1 * | 6/2004 | Carter et al. | 370/338 |
| 2004/0147818 A1 * | 7/2004 | Levy et al. | 600/300 |
| 2004/0151154 A1 * | 8/2004 | Wu | 370/349 |
| 2006/0206011 A1 * | 9/2006 | Higgins et al. | 600/300 |
| 2007/0098018 A1 * | 5/2007 | Kaler et al. | 370/477 |
| 2007/0135866 A1 * | 6/2007 | Baker et al. | 607/60 |
| 2007/0180140 A1 * | 8/2007 | Welch et al. | 709/238 |
| 2007/0255120 A1 * | 11/2007 | Rosnov | 600/300 |
| 2007/0255126 A1 * | 11/2007 | Moberg et al. | 600/365 |

FOREIGN PATENT DOCUMENTS

WO    02067122 A1    8/2002

* cited by examiner

*Primary Examiner* — Phung Nguyen

(57) ABSTRACT

A method and device for communicating physiological or control data between a portable device and an information system via telemetry. The system includes at least one portable device, and usually many, each having an I/O port for bidirectionally communicating physiological or control data in the form of IP data packets via telemetry. The portable device in operation includes a layered network interface that supports a standard internet-based networking protocol (IP) stack and PHY and MAC layers. The system also includes an information system connected to a wired network through a networking switch, and having a port for bidirectionally communicating data via telemetry with the portable device. The access point may include a program that converts the IP data packets between the RF PHY and MAC and network, such as Ethernet, PHY and MAC layers and further may include a server such as a BOOTP/DHCP server to support a dynamic assignment of an IP address to a number of portable devices.

20 Claims, 4 Drawing Sheets

INTERNET-PROTOCOL BASED TELEMETRY PATIENT MONITORING SYSTEM

CROSS REFERENCE TO RELATED APPLICATIONS

This application claims the benefit of U.S. provisional application Ser. No. 60/630,997 filed Nov. 24, 2004, which is incorporated herein by reference.

The invention relates to patient telemetry methods and devices.

Telemetry is well-known in the field of patient monitoring in medical facilities. For example, US Patent Publication 2004/0109429, published Jun. 10, 2004, discloses a wireless LAN architecture for various services within a medical facility. The same uses multiple WLAN protocols for wireless access. Similarly, PCT WO 02/067122 discloses a wireless telemetry monitoring system that connects to a wireless network and then to the Internet.

In prior art systems of these types, battery power for portable devices is at a premium. The battery power must be employed for powering very specific circuitry, not larger scale "general" circuitry, as this latter dissipates too much power, limiting battery life. Matched crystals are generally used to generate the RF connection, and the battery power is limited to powering only these and any necessary accompanying electronics.

Such systems include NBFM RF systems with frequency-paired transmitters and receivers. These systems employ a proprietary networking protocol that is tightly coupled with the RF system to transmit physiological and status information into an information system from the transmitter to the receiver.

Embodiments of the current invention provide a more sophisticated software architecture design for the portable devices employed for telemetry, and thus can run the more sophisticated—and more general and useful—Internet Protocol (IP) on the same. This architecture design is made possible in part by improvements in power performance from the portable device electronics, and by better and more general networking architecture systems for portable devices.

Embodiments of the system include a bidirectional, cellular-based, RF system that may employ DECT technology to implement the RF PHY and MAC. The system may operate within the WMTS telemetry monitor RF spectrum. On top of the RF PHY and MAC layers, the system abstracts data transport by implementing a standard TCP/UDP/IP/Ethernet networking stack to enable bi-directional transport of physiological and control information throughout the heterogeneous network, which may include both wired and wireless portions. Every portable device may be statically assigned an Ethernet MAC address and dynamically assigned an IP address to enable data communication within the network.

The system may be employed, e.g., within the PMS/CMS Intellivue® product family available from Philips Medical Systems of Andover, Mass. USA and Best, the Netherlands.

The system includes a method and device for communicating physiological or control data between a portable device and an information system via telemetry. The system includes at least one portable device, the portable device having an I/O port for bidirectionally communicating physiological or control data in the form of IP data packets via telemetry. The portable device in operation includes a layered network interface that supports a standard internet-based networking protocol stack and RF PHY and MAC layers. The system also includes an information system including at least one access point and an optional associated access pointer controller, connected to a wired network through a networking switch, and having an I/O port for bidirectionally communicating physiological or control data via telemetry with the portable device. The access point in operation includes a program that converts the IP data packets between the RF PHY and MAC and network, such as Ethernet, PHY and MAC layers and further includes a server such as a BOOTP/DHCP server to support a dynamic assignment of an IP address to the portable device.

Embodiments of the invention may employ adaptive compression based on the network headers as appropriate, e.g., UDP, IP, etc., for bandwidth optimization.

Advantages of embodiments of the invention are manifold. The use of standard networking protocols within telemetry monitoring reduces the cost of the network by allowing the use of standard networking infrastructure components. Management of the entire network is simplified, from portable device, to information system, by allowing the use of commonly available network management tools and services. The abstraction of the data communication protocol from the RF physical layer allows for the future swapping of the DECT-based RF PHY and MAC layers with other RF technologies, such as Zigbee, 802.15.1, 802.11a/b/g/e, NBFM, etc., without affecting the fundamental network architecture of the monitoring system. This approach decouples the portable device from a specific RF frequency and allows for the development of large-scale telemetry monitoring systems. The approach further allows other products, such as bedside monitors, defibrillators, etc., to easily be employed within the same RF and wired network as the portable telemetry devices.

Figure 1:
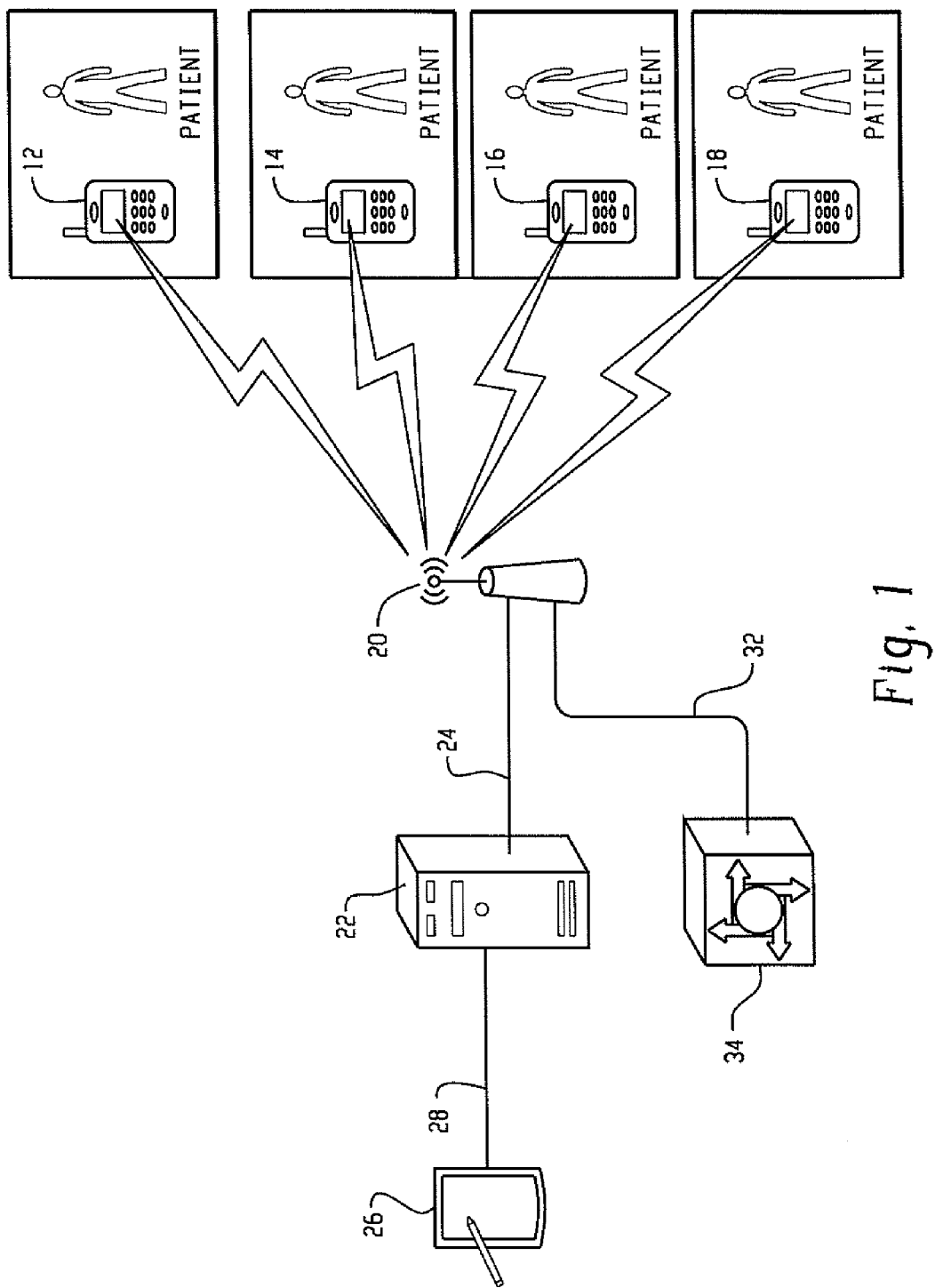
FIG. 1 shows a standard patient telemetry system, which may be within a house or medical facility.

A standard patient telemetry system is shown in FIG. 1. A plurality of portable telemetry devices 12-18 is shown in wireless, e.g., mobile, cellular, Zigbee, 802.15.1, 802.11a/b/g/e, NBFM, etc., communication with an access point 20. Portable telemetry devices 12-18 are typically battery-powered. Portable telemetry devices 12-18 transact IP data packets, bi-directionally, with an information system 22 via a connection 24 of the wired network. The data packets are typically real-time physiological and control information.

Portable telemetry devices 12-18 communicate with devices, e.g., tablet PC 26 on the wired network, e.g., via connection 28, through an access point 20. An optional access point controller 34 controls and directs the signals through access point 20 via a connection 32. The access point controller 34 may provide a control function for the access points and a routing function for the network data packets from the portable devices. It may be an independent device or it may be merged with the information system 22. The access point 20 and its associated access point controller 34 convert the IP data packets between, e.g., a DECT RF PHY and MAC and an Ethernet PHY and MAC. The access point 20 and its associated access point controller 34 are connected to the wired network via a standard networking switch (not shown). The information system 22 may be PC-based, and is connected to the wired network via a switch (not shown).

To support data transfer from the portable devices to the information system, the portable telemetry devices 12-18 implement in software a layered network interface that supports both a standard internet-based networking protocol stack, with, e.g., a BOOTP client service, and the RF PHY and MAC layers. The RF PHY and MAC layers may be implemented using DECT technology and may operate within the WMTS telemetry monitor RF spectrum. In this way, the portable devices 12-18 may wirelessly communicate data to the access point 20. Of course, future variants are not tied to DECT technology to support this function. Any appropriate wireless protocol may be employed. Nor are future variants tied to the WMTS telemetry monitor RF spectrum.

As noted, on top of RF PHY and MAC layers, the system abstracts data transport by implementing a standard TCP/UDP/IP/Ethernet networking stack to enable bidirectional transport of physiological and control information throughout the network (wired and wireless).

Figure 2:
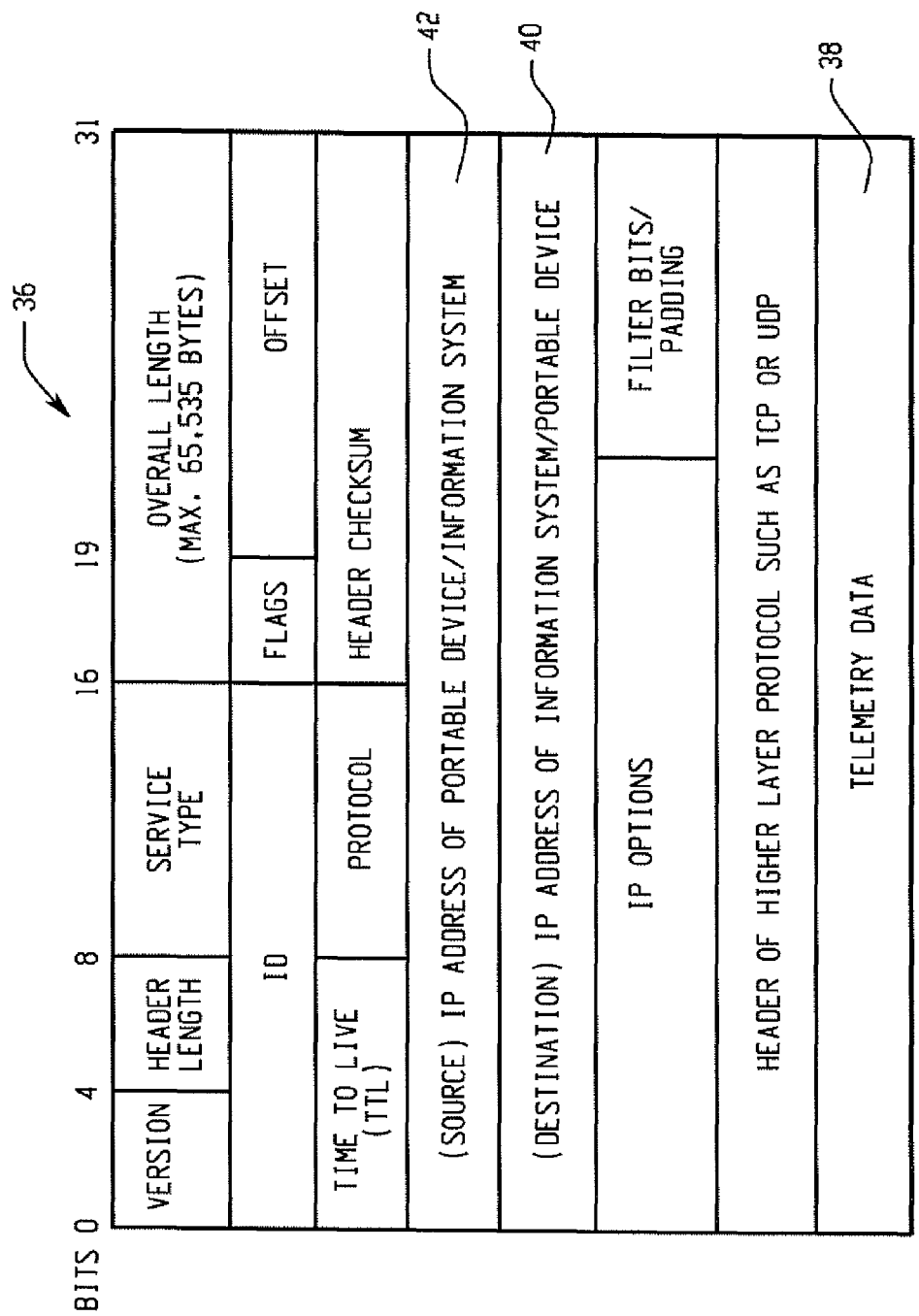
FIG. 2 shows a schematic of an IP data packet that may be employed within an embodiment of the present invention.

For example, as shown in FIG. 2, an IP data packet 36 appropriate for communication of physiological and control information is shown. One of portable devices 12-18 may measure a physiological value, and the same may be disposed in the data payload 38. The portable device may then wirelessly communicate the IP data packet 36 to the access point 20 using, e.g., DECT RF PHY and MAC layers. In so doing, the portable device imprints its source IP address on the IP data packet 26 as source address 42. The access point 20 may receive the IP data packet 36 and may further convert the same to Ethernet PHY and MAC layers. Once within the Ethernet PHY and MAC layer, the IP data packet 36 may be directed to the IP address indicated by a destination address 40, such as the information system 22.

To accomplish the addressing, especially dynamic addressing, the information system 22 may run a BOOTP/DHCP server to support the dynamic assignment of IP addresses for the portable devices 12-18. For example, access point controller 34 may also serve as the BOOTP/DHCP server in the system. Of course, it will be clear to one of ordinary skill in the art that any number of portable devices 12-18 may be employed, depending on the number of enduring IP addresses available to the system. In more detail, the portable devices may be dynamically assigned an IP address to enable communication within the network, as well as an Ethernet MAC address.

It should be noted here that the functions of access point 20 and access point controller 34 are flexible. The scheme in FIG. 1 may be employed, or the functions of access point controller 34 may be entirely contained with the access point 20 and/or the information system 22.

Figure 3:
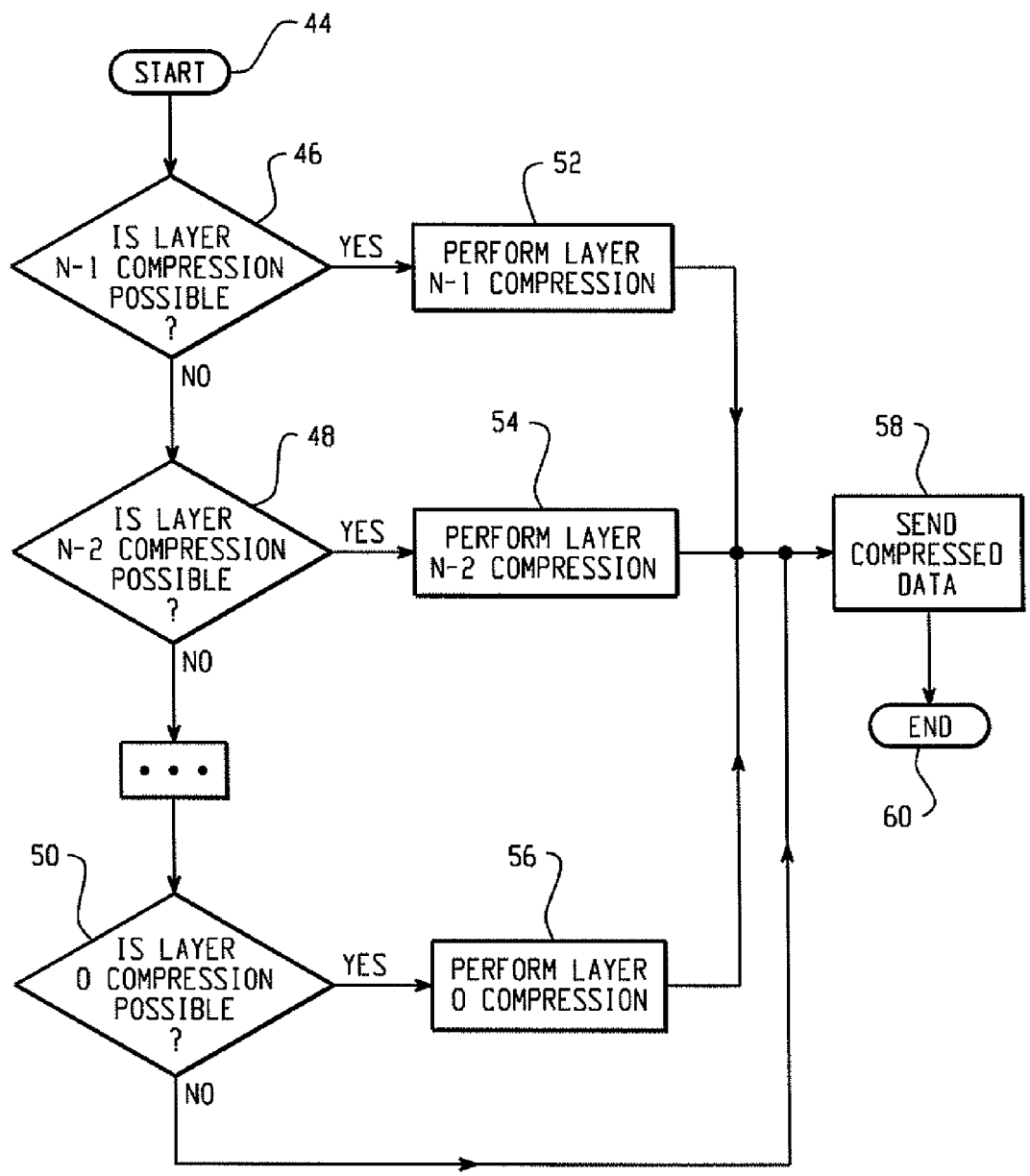
FIG. 3 shows a flowchart of an embodiment of the invention in which compression may be used for a layered network interface with N layers in the transmit path.

Referring to FIG. 3, an embodiment of the invention is shown in which adaptive compression specific to the network headers of the telemetric data packets is employed for a layered network interface with N layers in the transmit path. The compression is thus based on what type of data packet is used, e.g., UDP, IP, etc. This adaptive compression may be employed for bandwidth optimization, and is based on the detectable, uppermost layer in the network traffic, on a per packet basis. Such compression may apply to both the portable device, i.e., data from the measurement subsystems, and the access point, i.e., data from the wired network.

After a start step 44, which may simply be the last step of the immediately preceding algorithm, a determination is made as to whether a layer N-1 (of the network packets available for RF transmission) is compressible (step 46). If it is, compression is performed (step 52), and the data is sent on (step 58) and the process terminates (step 60). If it is not, a determination is made as to whether a layer N-2 is compressible (step 48). If it is, compression is performed (step 54), and the data is sent on (step 58) and the process terminates (step 60). This continues for all the layers until a determination is made as to whether a layer 0 is compressible (step 50). If it is, compression is performed (step 56), and the data is sent on (step 58) and in any case the process terminates here (step 60).

Figure 4:
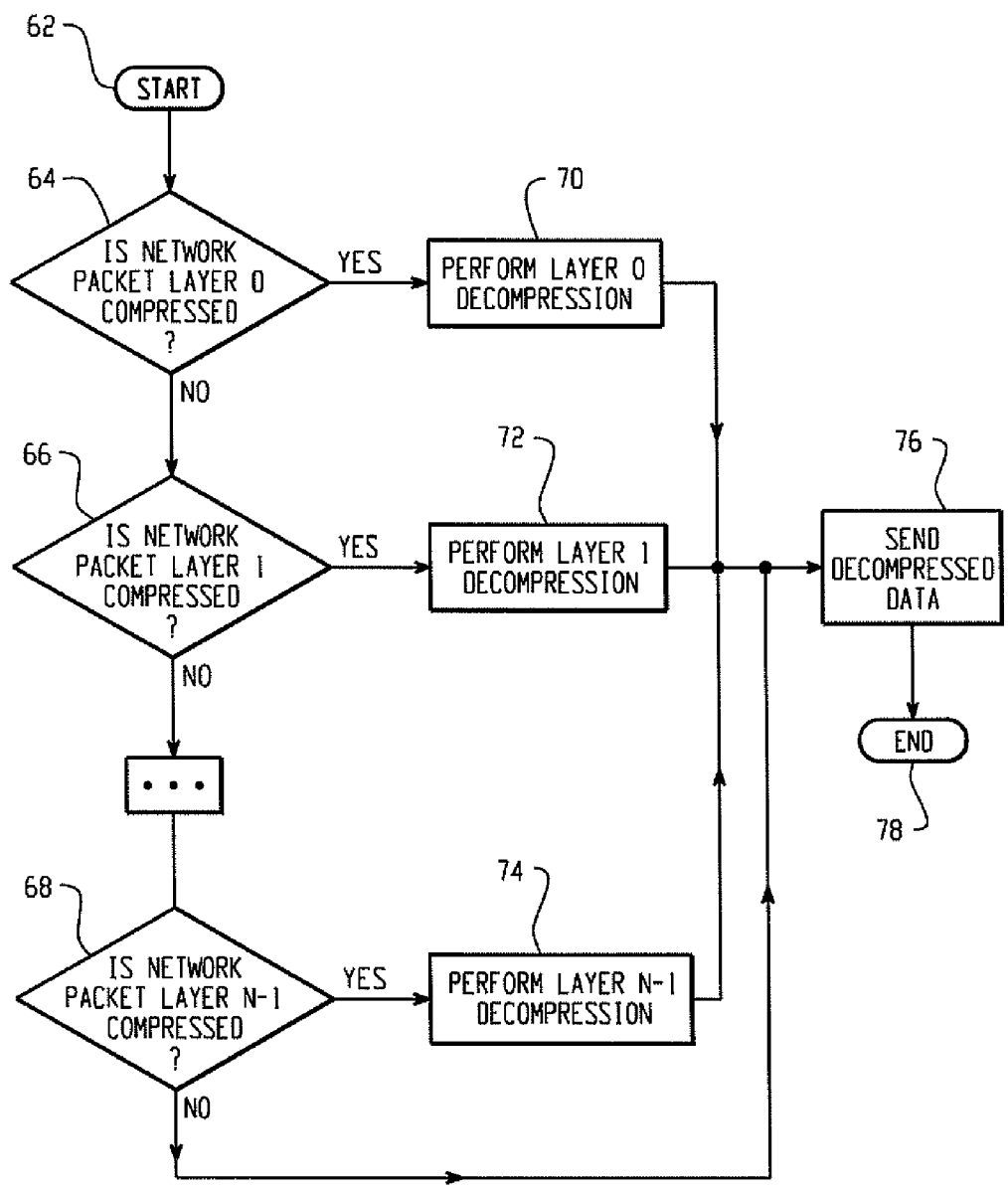
FIG. 4 shows a flowchart of an embodiment of the invention in which decompression may be used for a layered network interface with N layers in the receive path.

FIG. 4 shows a flowchart of an embodiment of the invention in which decompression may be used for a layered network interface with N layers in the receive path. The decompression is based on the encoding in the compression. Such procedures may apply to both the portable device and to the access point receiving data over the RF link.

After a start step 62, which again may simply be the last step of the immediately preceding algorithm, a determination is made as to whether a layer 0 packet (of a network packet received over RF) is compressed (step 64). If it is, decompression is performed (step 70), and the data is sent on (step 76) and the process terminates (step 78). If it is not, a determination is made as to whether a layer 1 packet is compressed (step 66). If it is, decompression is performed (step 72), and the data is sent on (step 76) and the process terminates (step 78). This continues for all the layers until a determination is made as to whether a layer N-1 packet is compressed (step 68). If it is, decompression is performed (step 74), and the data is sent on (step 76) and in any case the process terminates here (step 78).

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for communicating physiological or control data between a portable device and an information system via telemetry, comprising:
    at least one portable device, the portable device having an I/O port for bidirectionally communicating physiological or control data in the form of IP data packets via telemetry, wherein the portable device in operation includes a layered network interface that supports a standard internet-based networking protocol stack and RF PHY and MAC layers;
    an information system including at least one access point, connected to a wired network through a networking switch, and having an I/O port for bidirectionally communicating physiological or control data via telemetry with the portable device, wherein the access point and the portable device in operation includes a program that converts the IP data packets between the RF PHY and MAC and Ethernet PHY and MAC layers and further includes a server to support a dynamic or static assignment of a network identifier to the portable device.

2. The system of claim 1, wherein the RF PHY and MAC layers are DECT based.

3. The system of claim 1, wherein the RF PHY and MAC layers are selected from the group consisting of Zigbee, 802.15.1, and 802.11a/b/g/e.

4. The system of claim 1, wherein the portable device is battery-powered.

5. The system of claim 4, wherein the server includes a BOOTP/DHCP server which dynamically assigns an IP address to each portable device.

6. A system for communicating physiological and control data between a plurality of portable medical devices and an information system via telemetry, comprising:

each portable device having an I/O port for bidirectionally communicating physiological and control data in the form of IP data packets via telemetry, each portable device including a layered network interface that supports a standard internet-based networking protocol stack and has RF PHY and MAC layers;

an information system including at least one access point, connected to a wired network through a networking switch, and having an I/O port for bidirectionally communicating the physiological and control data via telemetry with the portable devices, the access point and the portable devices including a program that converts the IP data packets between the RF PHY and MAC layers and Ethernet PHY and MAC layers and a server which supports a dynamic or static assignment of a network identifier to the portable devices;

wherein at least one of (1) the portable devices and (2) the information system further includes a program for adaptive compression based on a network header of the physiological or control data.

7. The system of claim 6, wherein the adaptive compression includes:
   determining if each layer of the stack is compressible; and compressing each compressible layer individually.

8. The system of claim 7, wherein the adaptive compression further includes:
   decompressing each compressed layer individually.

9. The system of claim 6, wherein the adaptive compression includes:
   (a) determining whether a Nth layer of the stack is compressible;
   (b) in response to the Nth layer being determined to be compressible, compressing the Nth layer;
   (c) repeating steps (a) and (b) for each of a plurality of successively higher layers.

10. The system of claim 9, wherein the Nth layer is the lowest layer.

11. The system of claim 9, wherein the adaptive compression further includes:
    decompressing each compressed layer starting with a highest layer followed by decompressing each successively lower compressed layer.

12. A method for communicating physiological or control data between at least one portable devices and an information system via telemetry, comprising:
    bidirectionally communicating physiological and control data in the form of IP data packets via telemetry between each of a plurality of portable devices and an information system,
    with each of the plurality of portable devices, transmitting data using a standard internet-based networking protocol stack having a plurality of layers including RF PHY and MAC layers;
    with the information system, converting the IP data packets between the RF PHY and MAC layers and Ethernet PHY and MAC layers and dynamically or statically assigning a network identifier to each portable device;
    adaptively compressing the data based on a network header of the physiological or control data; and
    at least at the information system, decompressing the compressed data.

13. The method of claim 12, wherein the RF PHY and MAC layers are DECT based.

14. The method of claim 12, wherein the portable device is battery-powered.

15. The method of claim 12, wherein the converting the IP data packets between the RF PHY and MAC layers and Ethernet PHY and MAC layers includes converting the IP data packets to Ethernet PHY and MAC layers.

16. The method of claim 12, wherein assigning a network identifier to each portable device includes dynamically or statically assigning an IP address to each portable device.

17. The method of claim 12, wherein the compressing and decompressing steps are performed individually layer by layer.

18. The method of claim 12, wherein compressing the data includes:
    (a) determining whether a lower layer of the stack is compressible;
    (b) when the lower layer is determined to be compressible, compressing the lower layer;
    (c) repeating the determining and compressing steps (a) and (b) successively for each of a plurality of higher layers.

19. The method of claim 18, wherein the determining and compressing steps are performed from a lowest layer of the stack to a top layer of the stack.

20. The method of claim 12, wherein each portable device adaptively compresses the physiological data and decompresses the control data and the information system decompresses the physiological data and compresses the control data.

* * * * *